US006193413B1

(12) United States Patent
Lieberman (10) Patent No.: US 6,193,413 B1
(45) Date of Patent: Feb. 27, 2001

(54) SYSTEM AND METHOD FOR AN IMPROVED CALORIMETER FOR DETERMINING THERMODYNAMIC PROPERTIES OF CHEMICAL AND BIOLOGICAL REACTIONS

(76) Inventor: David S. Lieberman, 9192-C Regents Rd., La Jolla, CA (US) 92037

( * ) Notice: Subject to any disclaimer, the term of this patent is extended or adjusted under 35 U.S.C. 154(b) by 0 days.

(21) Appl. No.: 09/336,668

(22) Filed: Jun. 17, 1999

(51) Int. Cl.[7] .......................... G01N 25/00; G01N 25/20
(52) U.S. Cl. ......................... 374/45; 374/43; 374/45; 436/147; 436/157
(58) Field of Search ........................ 374/43, 45, 46, 374/14, 31, 35; 422/51, 109, 50; 436/147, 157

(56) References Cited

U.S. PATENT DOCUMENTS

| | | | |
|---|---|---|---|
| 3,765,237 | * 10/1973 | Blackmer et al. | 73/190 R |
| 3,789,662 | * 2/1974 | Zettler et al. | 374/31 |
| 4,095,453 | * 6/1978 | Woo | 73/15 B |
| 4,130,016 | * 12/1978 | Walker | 73/190 R |
| 4,166,016 | * 8/1979 | Paulen | 204/159.14 |
| 4,386,604 | * 6/1983 | Hershey | 128/718 |
| 4,672,561 | * 6/1987 | Katayama et al. | 374/31 |
| 4,783,174 | * 11/1988 | Gmelin et al. | 374/31 |
| 4,923,306 | * 5/1990 | Fauske | 374/34 |
| 5,163,753 | * 11/1992 | Whiting et al. | 374/10 |
| 5,451,371 | * 9/1995 | Zanini-Fisher et al. | 374/31 |
| 5,883,009 | * 3/1999 | Villa et al. | 438/739 |
| 5,967,659 | * 10/1999 | Plotnikov et al. | 374/31 |
| 6,017,465 | * 1/2000 | Naito | 252/299.01 |

OTHER PUBLICATIONS

Denlinger, et al., "Thin film microcalorimeter for heat capacity measurements from 1.5 to 800 K," American Institute of Physics, *Rev. Sci. Instrum.* 65 (4):946–959, (Apr., 1994).

* cited by examiner

*Primary Examiner*—G. Bradley Bennett
*Assistant Examiner*—Gail Verbitsky
(74) *Attorney, Agent, or Firm*—Lyon & Lyon LLP (57) ABSTRACT

A system and method for an improved calorimeter for determining thermodynamic properties of biological and chemical reactions. A microcalorimeter device comprises a thin amorphous membrane anchored to a frame. Thermometers and heaters are placed on one side of a thermal conduction layer mounted on the central portion of the membrane. An environmental chamber is vacated and humidified. First and second samples are placed on the membranes of first and second microcalorimeters. Each sample is heated and its individual heat capacity determined. The samples are then mixed by sandwiching the two microcalorimeters together to cause a binding reaction to occur. The enthalpy of binding is determined by measuring the amount of heat liberated during the reaction. The mixture is then heated and the heat capacity of the mixture is determined. From this data, a binding constant is calculated.

25 Claims, 6 Drawing Sheets

SYSTEM AND METHOD FOR AN IMPROVED CALORIMETER FOR DETERMINING THERMODYNAMIC PROPERTIES OF CHEMICAL AND BIOLOGICAL REACTIONS

This invention was made with Government support under NSF Grant No. BIR 9513629 awarded by the National Science Foundation. The Government has certain rights in this invention.

BACKGROUND OF THE INVENTION

1. Field of the Invention

The present invention relates generally to a system and method for an improved calorimeter, and more specifically, to a system and method for an improved calorimeter for determining thermodynamic properties of chemical and biological reactions.

2. Related Art

Heat absorption and/or heat release is ubiquitous to chemical and biological reactions. Thermodynamic information that characterizes these reactions is directly measurable through calorimetry. The thermodynamic information provides insight into the molecular forces that are driving the reactions.

Conventional calorimeters used to measure chemical and biological reactions generally comprise a fluid cell and an injection syringe. The fluid cell is loaded with a liquid receptor sample. One example of a receptor sample is a protein solution. The fluid cell is then placed within a cylindrical liquid filled chamber, where temperature measurements are subsequently made.

The injection syringe is loaded with a ligand, such as a drug that binds to the receptor sample when injected into the fluid cell. A known volume of the ligand solution is then injected into the fluid cell containing the receptor sample solution. When this occurs, the ligand and receptor sample solutions bind, which causes heat to be liberated.

Thermometers, within the cylindrical liquid filled chamber, precisely measure the amount of heat released during this process. This information is recorded, and the injection and measuring steps are repeated. This process continues until heat is no longer released. This indicates that all binding sites have been filled. Once the entire process is complete, scientists can determine thermodynamic properties associated with the two interacting molecules.

That is, because the exact volumes of the samples are known, as well as the precise amount of heat liberated, scientists can determine properties such as the equilibrium binding constant, the ratio of the participating molecules in the reaction (stoichiometry), and the heat of binding. Typically, these properties are determined by constructing a binding curve comprising multiple data points that are derived from each of the reactions as described above.

The problem with conventional chemical/biological calorimeters is that the above process is very meticulous and extremely time-consuming. In addition, the sensitivity of current systems is quite limited. For example, typically current systems cannot measure dissociation binding constants below $10^{-8}$ (or affinity binding constants above $10^8$). It is noted that the term "binding constant" is hereinafter defined as the dissociation constant. It would be desirable to increase the sensitivity of chemical/biological calorimeters so that lower binding constants can be detected and measured.

Further, current state of the art calorimeters require relatively large sample volumes on the order of one milliliter. Using these large sample volumes can be very expensive, especially for large-scale operations, such as high-throughput pharmaceutical drug screening and the like. Still further, current systems require that solutions are more dilute as the binding constants of the systems increase.

In addition, the large sample volumes required by current calorimeters preclude the study of certain phenomena. For example, many proteins, such as transcription factors, exist in relatively small amounts in the cell. Further, amplification is not possible until a gene is cloned and an expression system is developed. Consequently, scientists are precluded from studying the thermodynamic properties of such proteins using current systems.

Accordingly, what is needed is a system and method for determining thermodynamic properties of biological and chemical reactions that can be performed using lower volumes, can detect lower binding constants, and can be performed more efficiently and economically than conventional chemical/biological calorimeter systems.

SUMMARY OF THE INVENTION

Accordingly, the present invention is directed toward a system and method for determining thermodynamic properties of biological and chemical reactions that can be performed using much lower volumes and can detect lower binding constants than current systems. Further, the system and method of the present invention can be performed more efficiently and economically than conventional chemical/biological calorimeter systems. For example, to determine the equilibrium binding constant using conventional titration techniques involving multiple injections can take on the order of one hour to complete. Using the thermodynamic profiling technique as described below, equilibrium binding constants are calculated in seconds or minutes.

In operation, the present invention dramatically increases the sensitivity of calorimeters used to study chemical and biological systems. This includes thermodynamic study of protein-protein and protein-DNA interactions, the thermodynamics and kinetics of drug binding for both proteins and DNA, drug occupancy studies and studies of protein folding.

An advantage of the present invention is that it can measure samples that are at least 1000 times smaller than conventional systems. Further, an advantage of the present invention is that it can determine thermodynamic properties of samples with very high relative and absolute accuracy and from time resolved measurements.

Another feature is that many calorimeters can be made inexpensively due to the intrinsically parallel nature of semiconductor manufacturing techniques. Many novel applications lie in the ability to make large numbers of matched devices on a single wafer with interconnections built in. For example, in one embodiment, 24 devices fit on a four-inch wafer. In another embodiment, the devices are scaled down ten-fold, so that 2400 individual devices fit on a single wafer. Miniaturization of the devices to even smaller sizes is straightforward and depends solely on the fabrication techniques used to implement the present invention.

An advantage of the present invention is that it can measure both the heat capacity and the enthalpy of chemical and biological systems in a single experiment using a single device. In this fashion, binding constants can be derived much faster than conventional systems that require multiple experiments, such as conventional titration techniques using binding curve analysis.

As stated, the present invention requires much lower sample volumes for determining thermodynamic properties of chemical and biological systems. Specifically, sample volumes are in the nanoliter and smaller rather than the milliliter range as found in conventional systems. Thus, an advantage of the present invention is that it can accept sample volumes three orders of magnitude lower than is currently possible using conventional systems.

The smaller sample volumes and consequently faster thermal equilibration allow probing in shorter time domains than is presently possible. Unlike current chemical/biological calorimeters, one advantage of using the present invention is that it provides the ability to probe the time domain of heat release. This advantage allows for direct time-resolved thermodynamic characterizations. Thus, for example, the present invention can be used to determine the thermodynamic properties associated with protein folding, heat release of a single cell, the thermodynamic properties of molecular motors, molecular polymer assembly dynamics and enzymatic substrate turnover.

The present invention improves upon traditional applications such as differential scanning calorimetry and stopped-flow calorimetry. In addition, the present invention can be implemented using calorimeter arrays to facilitate and make possible large-scale operations, such as high-throughput pharmaceutical drug screening and the like.

The microcalorimeter of the present invention builds on existing microcalorimeters used in the electronics industry for measuring thin film samples of magnetic and superconducting materials. The present invention provides major improvements and modifications to such conventional microcalorimeters so that such systems can be used efficiently with chemical and biological systems.

Such improvements include an improved thermometer style to increase sensitivity over the much narrower temperature ranges needed for biological systems. For example, studies performed on biological systems are predominantly performed at room temperature, while studies using thin films range from around 4K to hundreds of degrees Celsius.

The present invention provides an environmental chamber that is vacated and humidified to control evaporation and the associated heat of vaporization. Additionally, the present invention provides an improved sample platform so that the microcalorimeters can be stacked (i.e. "sandwiched" together) to create a semi-adiabatic environment that is necessary for operation in saturated water vapor (unlike conventional system that operate in a vacuum). Further design improvements include creating arrays of devices on a single Silicon wafer for efficient large-scale operations.

The microcalorimeter of the present invention is preferably manufactured in a microelectronics fabrication facility. Specifically, the microcalorimeter device of the present invention comprises a thin amorphous Silicon Nitride ($Si_3N_4$) membrane anchored to a Silicon frame. A thermal conduction layer is deposited on the central portion of the membrane. Thermometers and heaters are on one side of the thermal conduction layer and samples are placed on the other. Standard microelectronic fabrication techniques are used to construct the microelectronic calorimeter device.

An environmental chamber is preferably configured to minimize thermal conduction from the calorimeter(s) therein. This is accomplished by removing the air from the chamber and then humidifying the chamber to a proper vapor pressure, so that the thermal link is only through the water vapor.

Water vapor pressure is monitored. One method to monitor water vapor pressure is by mounting a capacitance manometer to the chamber. Preferably, sample dispensing is accomplished through the use of robotics. A first sample is placed on the membrane of a first calorimeter. A second sample is placed on the membrane of a second calorimeter. The samples are combined by inverting one calorimeter and placing it on top of the second calorimeter. The surface tension is sufficient to keep the ultra-low volume samples from falling off the surfaces of the calorimeters.

In one embodiment, a clamshell is used to combine the first and second samples. A first calorimeter (or a set of calorimeters) is attached to one interior surface of the clamshell. A second calorimeter (or a set of calorimeters) is attached the other interior surface. The clamshell is configured such that the two sets of calorimeters are precisely aligned to mix the samples together when the clamshell is closed.

Binding constants for two interacting molecules are determined by first heating and determining the individual heat capacities of the samples before mixing. The samples are then mixed by sandwiching the two devices together to cause a binding reaction to occur. The enthalpy of binding is determined by measuring the amount of heat liberated or absorbed due to the binding reaction. The mixture is then heated and the heat capacity of the mixture is determined. From this data, the binding constant is calculated.

In one embodiment, a plurality of calorimeter devices is constructed onto two silicon wafers. Samples are placed on the each device and are mixed together by placing the first wafer in contract with the second wafer. The devices in the first layer are precisely aligned with devices in the second layer, so that when the wafers are combined, the individual devices are in alignment.

BRIEF DESCRIPTION OF THE FIGURES

The present invention is described with reference to the accompanying drawings, wherein.

In the figures, like reference numbers generally indicate identical, functionally similar, and/or structurally similar elements.

DETAILED DESCRIPTION OF THE PREFERRED EMBODIMENTS

The system and method of the present invention makes use of a modified version of a type of microcalorimeter used in the electronics industry to measure thin films. An example of such a device is described in the article entitled "Thin film microcalorimeter for heat capacity measurements from 1.5 to 800K" by Denlinger, et al., published by the American Institute of Physics in April 1994.

These devices have been used, for example, to analyze thin film recording material, such as magnesium oxide and the like. Similar devices have also been used in other applications, such as infrared night vision goggles, and for measuring background radiation in space. To the knowledge of the inventor, however, these devices have never been used to determine the thermodynamic properties of chemical and biological reactions, before the present invention.

Prior to the present invention, such microcalorimeters required the use of a vacuum to reduce the thermal conductance between the sample area and the surrounding environment. Biological systems are typically based in aqueous solutions and would evaporate in a vacuum. Thus, these microcalorimeters are incompatible with chemical and biological systems.

However the present invention provides extensive modifications and improvements to the above systems. For example, the present invention provides an environmental chamber comprising a saturated environment that makes it possible to use with chemical and biological system. This improvement and other modifications and improvements are described in detail below.

Figure 1A:
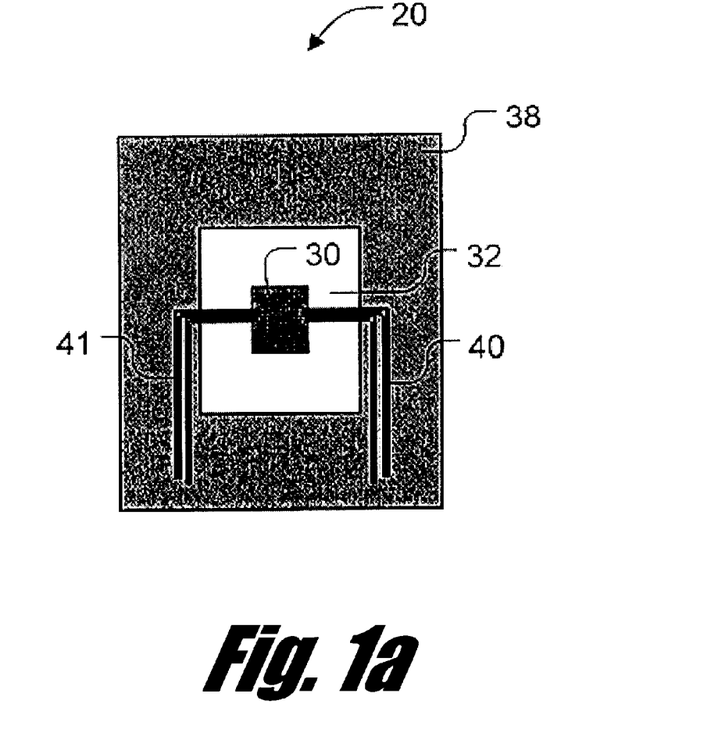
FIG. 1 is a block diagram depicting the components of a microcalorimeter in accordance with one embodiment of the present invention.
Figure 1B:
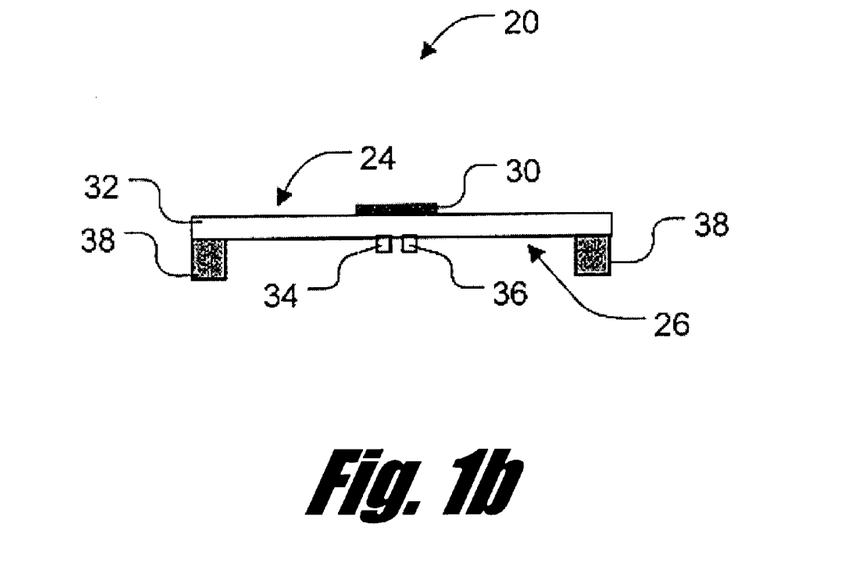

FIG. 1 is a block diagram depicting the components of a microcalorimeter in accordance with one embodiment of the present invention. This device is also referred to herein as a "microelectronic calorimeter." In the upper portion of FIG. 1, a top view of the microcalorimeter 20 is shown. In the lower portion of FIG. 1, a side view of the microcalorimeter 20 is shown.

The microcalorimeter 20 comprises a thin amorphous Silicon Nitride ($Si_3N_4$) membrane 32 anchored to a Silicon frame 38. In this example embodiment, the dimensions of the silicon frame are 1×1 $cm^2$ and the dimensions of the membrane 32 are 0.5×0.5 $cm^2$. The membrane 32 in this example is 1800 Å thick. In another embodiment, a plurality of calorimeters 20 is fabricated on a single silicon wafer, wherein each calorimeter 20 is the same size or smaller than the dimensions described in the example above. This is referred to as a calorimeter array and is described below with reference to FIG. 6.

A thin thermal conduction layer 30 is deposited on the central portion of the membrane 32 using standard microelectronic fabrication techniques. The top surface of the conduction layer is where samples are placed. In this example, the thermal conduction layer 30 is 0.25×0.25 $cm^2$. In this example embodiment, the conduction layer 30 is made of gold. In other embodiments, different metals can be used, but ideally, materials with lower thermal diffusions are preferred. In addition, gold is preferred due to its biological compatible properties.

It is noted that the materials used to describe a preferred embodiment of the present invention are used for exemplary purposes only. In other embodiments, different materials are used. For example, Silicon Carbide can be used to implement the thin membrane 32. Glass or quartz can be used to implement the frame 38. In another embodiment, mylar and metal can be used to implement the membrane 32 and the frame 38, respectively. Thus, the use of the materials used to describe the example embodiment presented herein should not be construed to limit the scope and breadth of the present invention.

It is noted that a membrane 32 is used in the example embodiment to thermally isolate the conduction layer 30 (i.e. sample holder). However, any means to thermally isolate the sample holder can be used in alternate embodiments of the present invention. Accordingly, the use of the membrane 32 in the preferred embodiments described herein should not be construed to limit the scope and breadth of the present invention.

It is noted that a heater 34 is used in the example embodiment as an energy input device to stimulate the sample(s). In other embodiments, other types of energy input devices can be used. For example, any type of electromagnetic radiation can be used to stimulate samples(s). Accordingly, the use of the heater 34 as the energy input device in the examples herein, should not be construed to limit the scope and breadth of the present invention.

A heater 34 and a thermometer 36 are placed on the bottom portion of the conduction layer 30, using standard microelectronic fabrication techniques. For example, in one embodiment, a quartz thermometer is attached to the bottom portion of the conduction layer 30 using standard microelectronic fabrication techniques. Similarly, a metal heater, such as a nickel resistance-type heater 34 is patterned in close proximity to the thermometer 36. As described below, the heater 34 is used to heat the samples, and the thermometer 36 is used to precisely measure the heat difference (i.e. heat release or absorption) of the sample. A pair of leads 40 and 41 are attached to the thermometer 36 and the heater 34, respectively.

To detect and accurately measure temperature changes in small volume samples, it is preferred that small thermal masses be used to implement the sample holder 30, the thermometer 34 and the heater 36. This is accomplished by the use of silicon micromachining to make an extremely thin film membrane 32 that can support thermometry on one face 26 and the sample on the other 30.

The high aspect ratio of the membrane 32 provides for fast thermal equilibration with the thermometer 34 and slow thermal equilibration with the surrounding silicon frame 38. This thermally isolates the sample. However, thermal isolation alone is not sufficient to make a precision calorimeter device. Equally important is the thermometry used which determines how sensitive the calorimeter is to heat effects. To satisfy both the high sensitivity and time resolution requirements, a preferred embodiment of the present invention uses an oscillator-thermometer rather than standard thermometer devices.

Standard thermometers rely on measuring a voltage change due to some material property in the thermometer, such as a resistance change or the like. This technique however, is not the preferred method in accordance with the present invention. An oscillator that relies on measuring the resonant frequency of an acoustic wave generated in the thermometer 36 of the calorimeter 20 is the basis for the technique used in a preferred embodiment of the present invention. Using this technique, the frequency of the acoustic wave depends on the velocity of the acoustic wave, which depends on temperature.

An embodiment of the present invention preferably uses a modulation domain analyzer for frequency counting. A modulation domain analyzer is a class of instrument that counts frequencies, for example, up to 12 digits per second. This provides both sensitivity and time resolution far beyond the capabilities of conventional resistive thermometers.

The idea behind the measurement scheme is to maximize the sensitivity by making use of modulation domain analyzers, as stated above. These instruments can be thought of as frequency oscilloscopes that measure frequency vs. time. Modulation domain analyzers generally use one of two methods for counting frequency with no dead time between measurements.

The Linear interpolation method uses charging capacitors to keep track of accumulated time between start and stop signals. The Vernier interpolation method is a digital method that uses several clocks, one pair of which is offset in frequency by 1+1/n from a reference clock.

The Vernier interpolation method is becoming the dominant method used in commercial modulation domain analyzers available today. Some have single shot resolution of 12 digits/sec (i.e. $1:10^{12}$ in 1 sec with no averaging). To take further advantage of this technique, sensitivity can be improved by beating down the frequency of the oscillators to thereby reduce the number of digits to count, and thus keeping a high sensitivity even in short (biologically relevant) timing windows.

The above technique is referred to as heterodyning. It involves mixing the oscillator with another oscillator and filtering out the high frequency components. This results in an output frequency defined by the difference between the frequency of the two oscillators. In this fashion, where both oscillators are in contact with the same sample, this technique has the effect to double the temperature resolution. The following example illustrates this technique.

Assume that an oscillator with a resonant freq (f) of 10 MHz, has a temperature sensitivity of 100 ppm/K. Thus, a $\Delta T$ of $1K=\Delta f$ of 1000 Hz. Further assume that a device can read 10 digits/sec (single shot). This corresponds to a 1 mhz frequency resolution/sec=1 $\mu K$/sec.

Using the technique described above, the oscillators are beat down from 10 Mhz to 100 khz. In this example, to get the same 1 mhz resolution now takes only 10 ms. Thus, going to higher frequencies increases the temperature sensitivity. In a preferred embodiment of the present invention, two or more oscillators that are in contact with the same solution are used to produce an increase in sensitivity.

Figure 2:
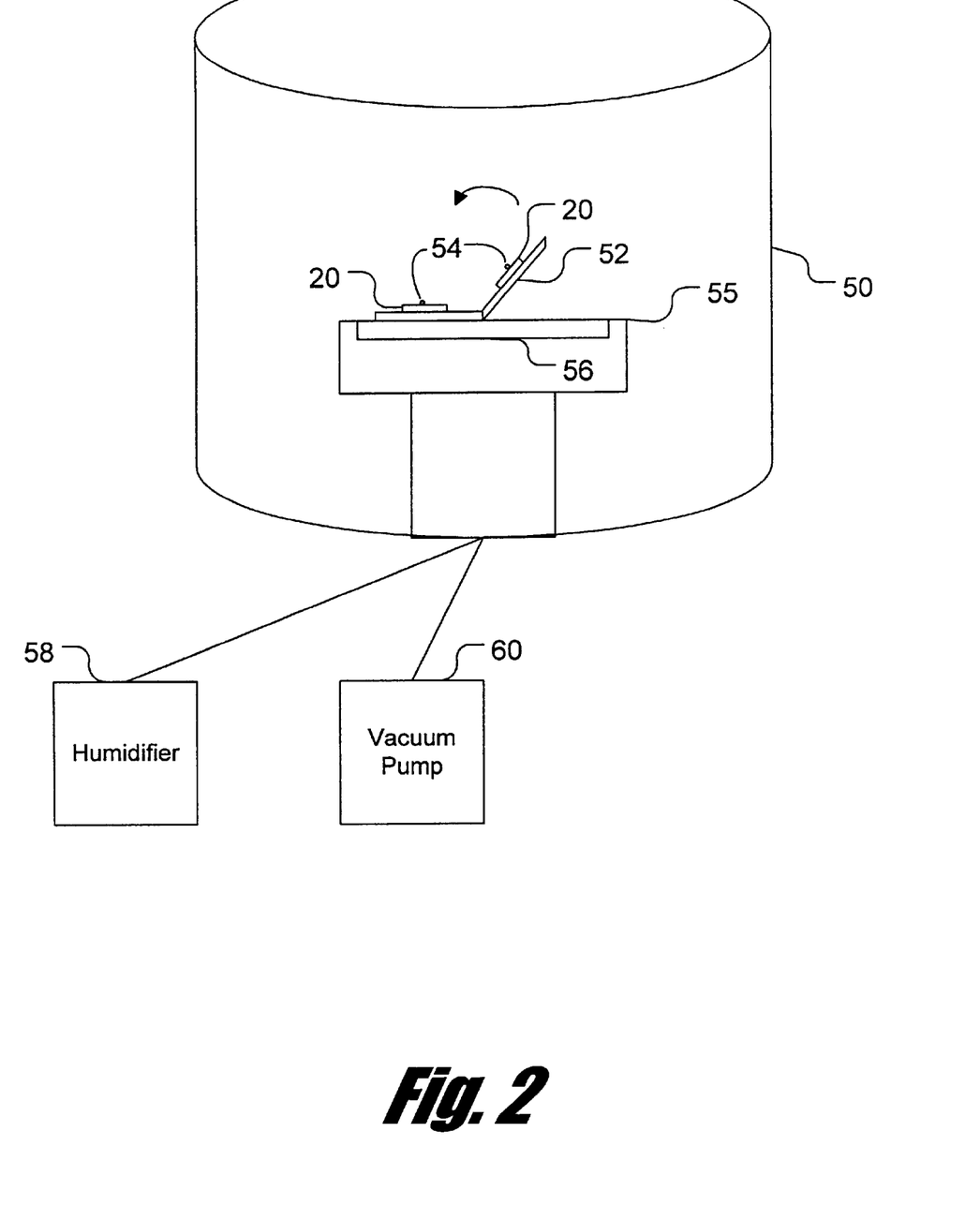
FIG. 2 depicts and example environment in accordance with the system and method of the present invention.

FIG. 2 depicts and example environment in accordance with the system and method of the present invention. As shown in this example embodiment, two microcalorimeters 20 are attached to a clamshell device 52. A sample 54 is placed on each of the microcalorimeters 20. Generally, this is accomplished by robotic means using any type remotely controlled ultra low volume dispensing device. The purpose of the clamshell device 52 is to mix the samples 43 when the clamshell 52 is closed in the direction of the arrow shown in FIG. 2.

The clamshell device 52 in this example is placed on a platform 55. A heating device is attached to the platform 55 to control the environmental temperature of the experiment. Typically, electronically controlled devices (not shown) are used to control the closing of the clamshell 52 to mix the samples 54 from the two calorimeters 20.

The platform 55 is placed in an environmental chamber 50. The chamber 50 is configured to minimize thermal conduction from the calorimeters 20. This is accomplished in this example embodiment, by using a humidifier 58 and a vacuum pump 60 attached to the chamber 50. The pump 60 is used to extract air from the chamber. The humidifier 58 is used to humidify the environment inside the chamber 50.

Accordingly, reducing thermal conduction from the calorimeters 20 is accomplished by removing the air from the chamber using the vacuum pump 60, and then humidifying the chamber using the humidifier 58. The chamber is humidified to a proper vapor pressure so that the thermal link from the calorimeter 20 is only through the water vapor. Alternatively, operation can occur in air or gas with the proper water vapor pressure. Using this alternative method, the thermal link is determined experimentally so that it can be compensated for when determining the thermodynamic properties of the sample(s).

In a preferred embodiment, the same aqueous solution used to contain the samples 54 is used as the humidifying agent in the humidifier 56. In this fashion, the vapor pressures of the chamber 50 closely matches the vapor pressure of the samples 54, to avoid evaporation. Generally, the vapor pressure of the samples must be within a predetermined threshold from the vapor pressure of the chamber to avoid evaporation.

In a preferred embodiment of the present invention, a capacitance manometer (not shown) is mounted to the chamber 50 and is used to monitor water vapor pressure therein. As stated, sample dispensing is accomplished robotically using vacuum compatible stages (not shown). In one embodiment, the clamshell device is manually closed using a wobble stick or the like. In another embodiment, robotic devices are used to close the clamshell device 52. A piezo actuator or the like (not shown) is used to close the gap between the top and bottom set of calorimeters 20 when the clamshell 53 is in the closed position.

The rate of the actuation of the piezo actuator can be varied. In one example, the rate of the actuation is from ~100 $\mu s$–800 $\mu s$. In other embodiment, the gap can be closed slower or faster. For example, in one embodiment, the gap is closed slower by setting a ramp rate for the voltage source, which is preferably computer controlled.

The actuation displacement can be monitored, for example, by using a Linear Variable Differential Transformer with a resolution of around 250 Å mounted at the end of the piezo actuator. In a preferred embodiment, a silicon diode (not shown) is mounted on the sample platform 55 to monitor temperature. The temperature controller can use the input of this thermometer to control power to a heater 56 also mounted on the platform 55.

Figure 3A:
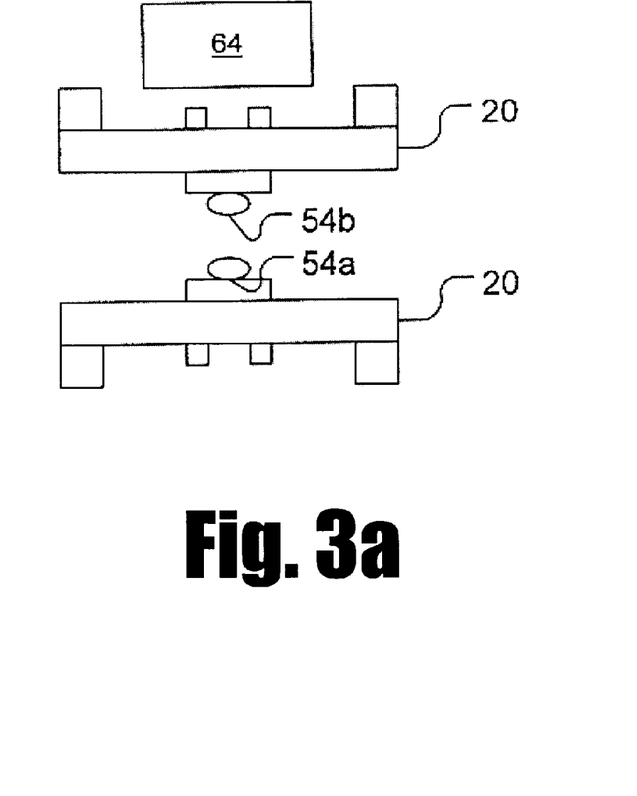
FIG. 3 is a block diagram depicting a preferred means for mixing samples together in a preferred embodiment of the present invention.
Figure 3B:
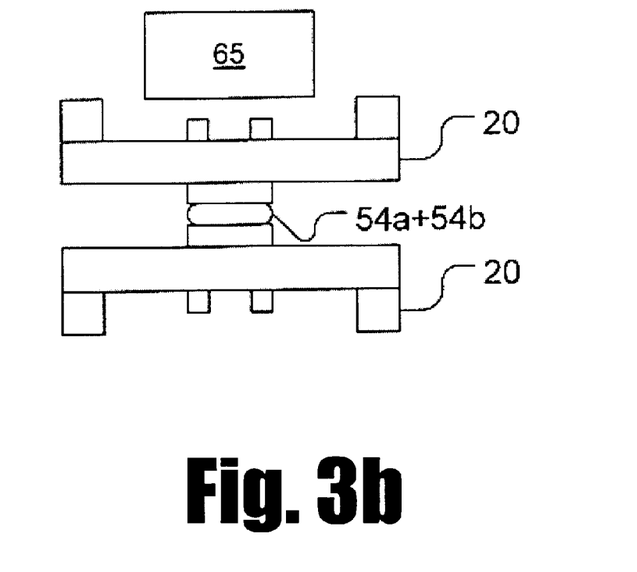

FIG. 3 is a block diagram depicting a preferred means for mixing samples in a preferred embodiment of the present invention. As shown in block 64, the samples 54a and 54b are each placed on a microcalorimeter device 20. As shown, one of the microcalorimeters 20 is positioned such that the two microcalorimeters 20 face each other. Due to the ultra small volumes used, the surface tension between the sample 54 and the conduction layer 30 is sufficient to hold the samples in any inverted position. The orientation of the pair of microcalorimeters 20 is irrelevant. The examples described herein depicting a horizontal orientation for a preferred embodiment of the present invention is for exemplary purposes only. In other embodiments, the microcalorimeters 20 are oriented in a vertical configuration. In yet other embodiments, the microcalorimeters 20 are oriented in configurations between the vertical and horizontal configurations as described above. The important point is that the microcalorimeters 20 are positioned such that they face each other, as shown in FIG. 3.

Block 65 depicts a preferred method for mixing the samples 54a and 54b together. In order to mix the samples 54a and 54b, the microcalorimeters 20 are moved in close proximity to each other, such the samples combine as shown in 54a+54b. This method of mixing as shown in FIG. 3 has several advantages over a method in which the second sample is injected or dropped on top of the first sample.

However, the selection of which mixing method to use, depends on the experiment being performed. For example, when performing the thermodynamic profiling method, as described below, the mixing method shown in FIG. 3 is preferred in order to avoid erroneous calculations.

For example, by dropping a second sample on top of a first sample errors in the dispensed volume will introduce erroneous results when a second heat capacity measurement (on the mixture) is performed. Instead, using the mixing method depicted in FIG. 3, no errors are introduced because the heat capacity is determined before and after the sample mixing and the heat capacity depends on mass. Accordingly, using the preferred mixing method shown in FIG. 3, there is no volume change before and after the mixing process. Thus, there are no heat capacity errors associated with the uncertainties in the volume of the added solution.

However, for some applications, the first technique of mixing solutions by dropping a second solution on top of a first solution can be used. For example, when determining enzyme/substrate inhibition, the simpler mixing technique can be used to avoid an unnecessarily complicated experiment.

As described below, an advantage to using separate microcalorimeters 20 for each of samples 54a and 54b, and the use of the mixing technique shown in FIG. 3, provides the ability of determining the binding constant in a single experiment, as described below. This technique is referred to herein as the "thermodynamic profiling" technique, method or process in accordance with a preferred embodiment of the present invention.

A method of determining the binding constant and other thermodynamic properties using the thermodynamic profiling technique in accordance with a preferred the present invention will now be described with reference to FIG. 4.

Conventionally, titration calorimetry is the method used for determining the equilibrium binding constant ($K_d$) of 2 interacting molecules. The method determines the equilibrium binding constant through the relationship:

$$K_d = [L][P]/[LP] \quad \text{Equation (1)}$$

where:
 $K_d$=dissociation equilibrium binding constant
 L=concentration of first sample (i.e. drug or protein or DNA, etc.)
 P=concentration of second (receptor) sample, (i.e. protein, DNA, etc.)
 LP=concentration of the bound complex This method suffers from the fact that the range of $K_d$ values that can be accurately determined is limited by the need to have increasingly dilute solutions of the samples as the $K_d$ gets lower. This sets the lower limit of the $K_d$ that titration calorimeters can access. In addition, another limitation of using this method is that it requires that timely multiple injections are performed in order to construct a binding curve to determine the equilibrium binding constant.

Unlike conventional systems and methods, the present invention makes use of a different relationship to determine the equilibrium binding constant. Namely, the relationship:

$$K_d = e^{-\Delta G/RT} \quad \text{Equation (2).}$$

Equation (2) can be re-written in the form:

$$\ln[K_d] = -\Delta H/RT + \Delta S/R \quad \text{Equation (2a).}$$

where:
 $K_d$=equilibrium binding constant
 $\Delta H$=binding enthalpy
 $\Delta S$=binding entropy
 T=temperature
 R=gas constant Equation (2) has not been used conventionally to determine equilibrium binding constants because the determination of the parameters in the $\Delta H$ and $\Delta S$ were not previously possible using a single experiment. However, as would be appreciated by persons skilled in the relevant art(s), the present invention provides the ability to determine the binding enthalpy ($\Delta H$) and binding entropy ($\Delta S$), and hence $K_d$, using a single device in a single experiment.

It should be noted that traditional methods using titration calorimetry techniques first determine $K_d$ and $\Delta H$. From that information, $\Delta S$ is then calculated. Using these conventional methods to determine the heat capacity ($\Delta C_p$) through titration calorimetry, experiments need to be performed at several temperatures. However, as described below, the method and system of the present invention provides the ability to determine the heat capacity using a single temperature and thus, a single experiment. This procedure, referred to as the thermodynamic profiling technique, is described in detail below.

It is noted that there are no concentration dependencies in equation (2). Therefore, an advantage to using this equation is that concentrations can be optimally increased to increase the signal to noise ratio. This allows for less expensive and complex thermometers to be used with an embodiment of the present invention.

It is noted that heat capacities, entropies and enthalpies are thermodynamic state functions and are additive. Accordingly, the binding reaction enthalpies, entropies, and heat capacities are equal to the difference between the initial states and final states of the respective functions for a particular substance. Stated mathematically:

$$\Delta C_p = C_{p(final)} - C_{p(initial)} \quad \text{Equation (3)}$$

$$\Delta S = S_{(final)} - S_{(initial)} \quad \text{Equation (4)}$$

$$\Delta H = H_{(final)} - H_{(initial)} \quad \text{Equation (5)}$$

Accordingly, to determine the equilibrium binding constant using the thermodynamic profiling method, the following relationship is used:

$$S = C_p (\ln T_2/T_1) \quad \text{Equation (6)}$$

Accordingly, equation (6) is used to determine $\Delta S$ for the reaction where the $C_p$ is directly determined by heating the samples (as described below). Further, in a preferred embodiment, the experiment is controlled such that all temperatures $T_2$'s are equal to each other and all $T_1$'s are equal to each other. Further, in a preferred embodiment, it is desirable set $T_1$ as close as possible to $T_2$. Generally, $T_1$ is the controlled by the platform heater 55 and $T_2$ is controlled by the heater 36 on the calorimeter 20. Thus, $\Delta H$ is determined directly from the heat released or absorbed from mixing the reactants. This procedure is described below with reference to FIGS. 4 and 5.

Figure 4A:
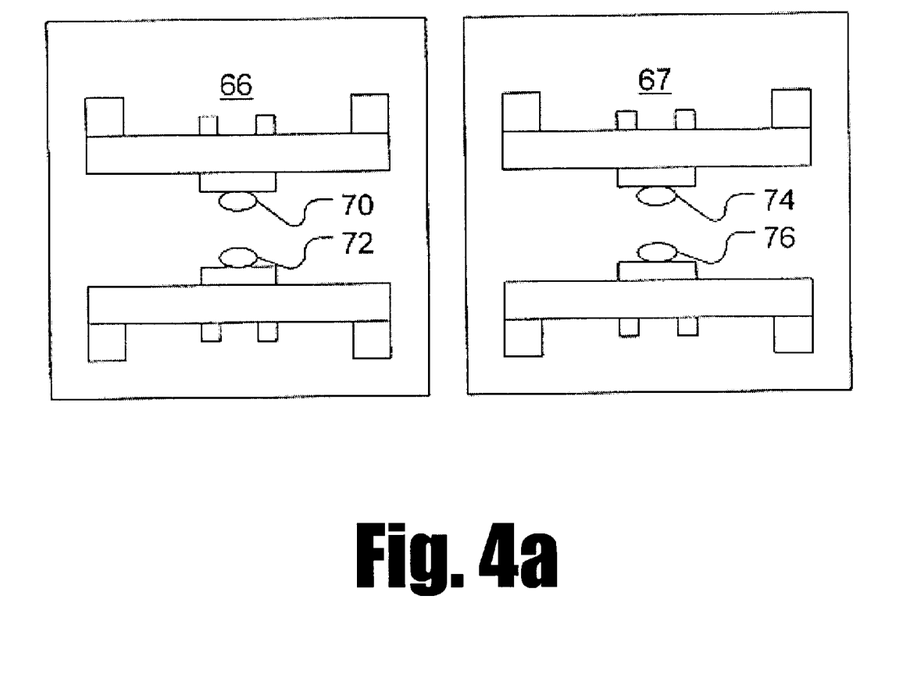
FIG. 4 is a block diagram useful for describing a preferred method of determining the binding constant and other thermodynamic properties using the thermodynamic profiling technique in accordance with an embodiment of the present invention.
Figure 4B:
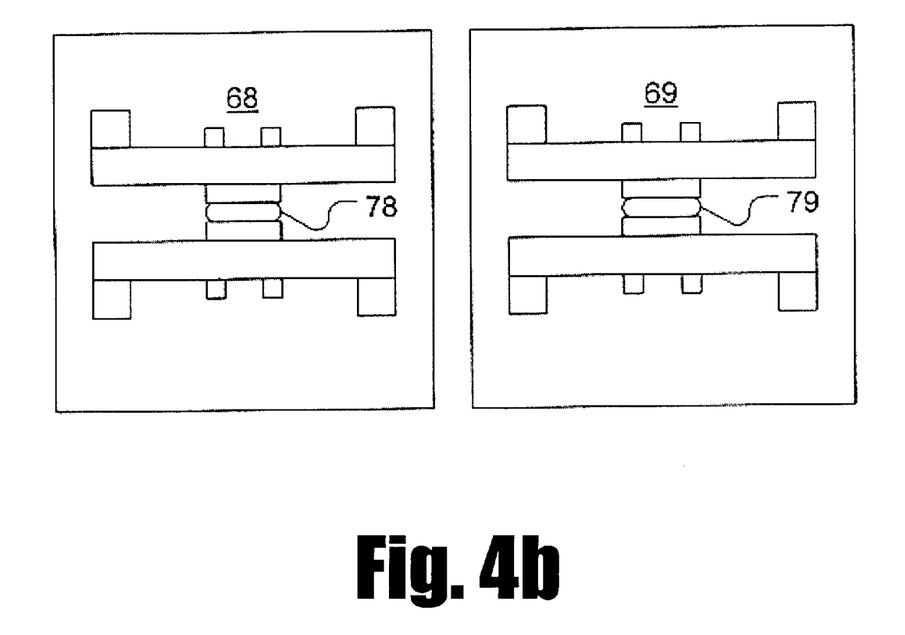

FIG. 4 depicts an example showing the various stages of an example experiment using two pairs of microcalorimeters. The pair or microcalorimeters on the right (67 and 69) are used to hold reference samples 74 and 76. The pair or microcalorimeters on the left (66 and 68) are used to hold samples of interest 70 and 72.

The pairs of microcalorimeters are shown at two points in time. Specifically, block 66 represents a point in time before the samples 70, 72 are mixed and the block 68 represents a point in time after the samples are mixed to produce the mixture 78. Similarly, block 67 represents a point in time before the reference samples 74 and 76 are mixed, and the block 69 represents a point in time after the samples are mixed to produce the mixture 79.

The first set of microcalorimeters 66 is loaded with two samples of interest 70 and 72, such as a ligand and a protein solution. The second set of microcalorimeters 67 is loaded with a pair of reference samples 74 and 76.

Accordingly, the top half of FIG. 4 (66 and 67) represents the sample pairs before the microcalorimeters are brought together for mixing purposes, and the bottom half (68 and 69) represents the sample pairs after mixing. In the equations below, the subscripts indicate the associated sample or mixture. For example $S_{70}$ refers to the entropy associated with sample 70. Similarly, $S_{78}$ refers to the entropy associated with the mixture 78. This example is used to describe the thermodynamic profiling process in accordance with a preferred embodiment of the present invention.

First, it is noted that the entropy of each sample before they are mixed is expressed as:

$$S_{70} = C_{p70} \text{Ln} \frac{T_2}{T_1}, S_{72} = C_{p72} \text{Ln} \frac{T_2}{T_1},$$
$$S_{74} = C_{p74} \text{Ln} \frac{T_2}{T_1} \text{ and } S_{76} = C_{p76} \text{Ln} \frac{T_2}{T_1},$$

where $T_1$ and $T_2$ are the temperatures of the associated samples when the specific heat is measured. For example, using the relaxation method, a sample is heated to $T_2$ and allowed to cool to $T_1$. It is noted that in this example, the relaxation method for determining the specific heat is used to simplify the description herein. However, in a preferred embodiment of the present invention, the well-known A/C method the preferred method for determining the specific heat(s) of the sample(s).

Thus, because the specific heats are additive:

$$\Delta S_{70,74} = C_{p70} \text{Ln} \frac{T_2}{T_1} - C_{p74} \text{Ln} \frac{T_2}{T_1} \text{ and}$$
$$\Delta S_{72,76} = C_{p72} \text{Ln} \frac{T_2}{T_1} - C_{p76} \text{Ln} \frac{T_2}{T_1}$$

Because we know the reference sample has no binding reaction, the equation becomes:

$$\left( C_{p78} \text{Ln} \frac{T_2}{T_1} - C_{p79} \text{Ln} \frac{T_2}{T_1} \right) -$$
$$\left( C_{p70} \text{Ln} \frac{T_2}{T_1} - C_{p74} \text{Ln} \frac{T_2}{T_1} + C_{p72} \text{Ln} \frac{T_2}{T_1} - C_{p76} \text{Ln} \frac{T_2}{T_1} \right) = \Delta S_{reaction}$$

Because all $T_1$'s are the same, and all $T_2$'s are the same, this simplifies to become:

$$\text{Ln} \frac{T_2}{T_1} (C_{p78} - C_{p79} - C_{p70} + C_{p74} - C_{p72} + C_{p76}) = \quad \text{Equation (7)}$$
$$\Delta S_{reaction}.$$

Figure 5:
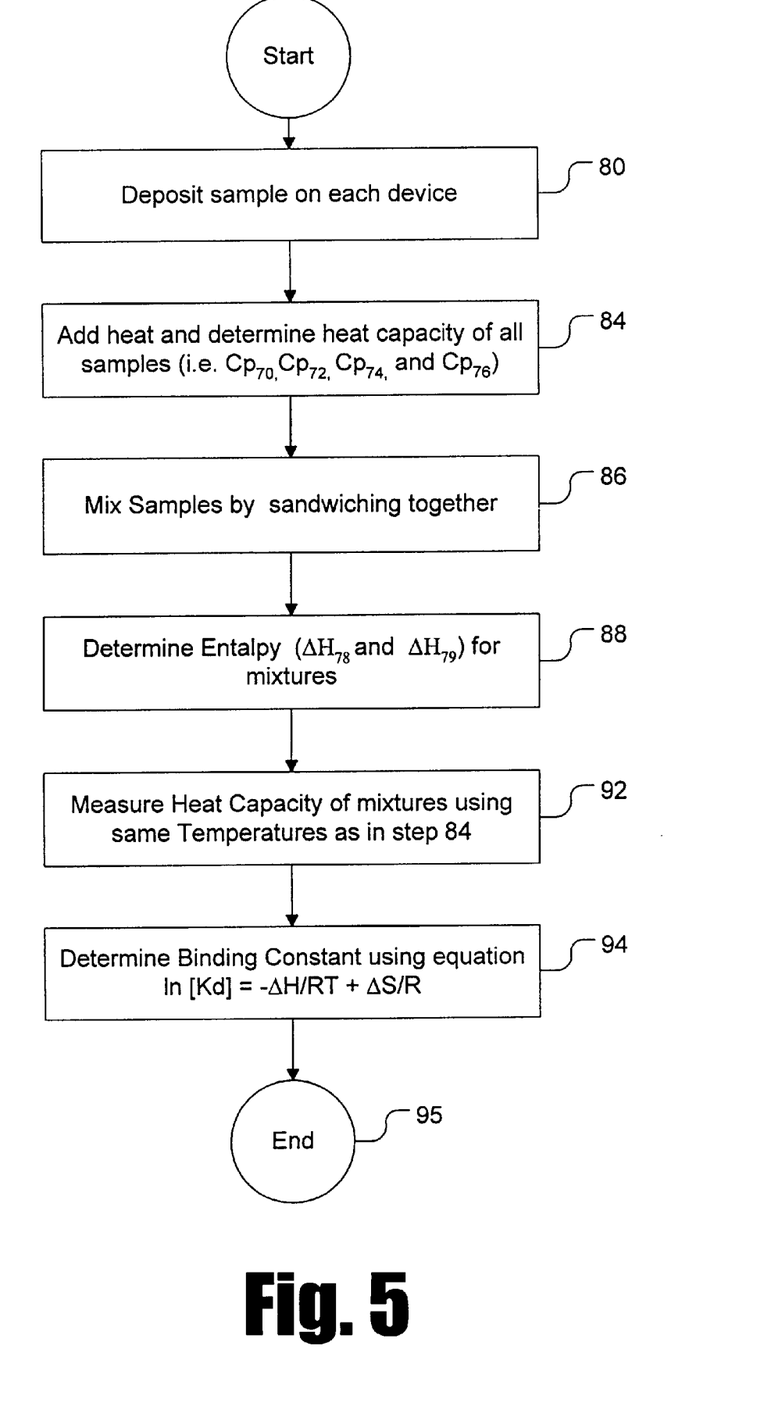
FIG. 5 is a flowchart depicting a process that can be used to determine the equilibrium binding constant of two interacting molecules using the thermodynamic profiling technique in accordance with a preferred embodiment of the present invention.

FIG. 5 is a flowchart depicting a process that can be used to determine the equilibrium binding constant of two interacting molecules using the thermodynamic profiling technique in accordance with a preferred embodiment of the present invention.

The process begins with step 80, where the samples are deposited on each microcalorimeter 20 device. Next, in step 84, heat is added to each device in a process to measure the heat capacity of each sample before they are mixed. For example, using the above example experiment, the heat capacity for the samples 70, 72, 74 and 76 are determined. In a preferred embodiment, the temperatures are selected such that all $T_1$'s are equal and all $T_2$'s are equal Next in step 86, the samples are mixed together. Again using the example experiment above, this forms the mixtures 78 and 79. It should be noted that the use of one sample pair of interest and one reference sample pair is used for exemplary purposes only to particularly point out the features and functionality of the present invention. In other embodiments, different configurations can be used. For example, in one embodiment, more than one pair of reference samples is used to obtain more accurate results. In any case, the use of reference samples in experiments to determine thermodynamic properties is well known and such use would be apparent to persons skilled in the relevant art(s). As such, the use of one sample pair and one reference pair in the examples herein should not be construed to limit the scope and breadth of the present invention.

Next as indicated in step 88 the Enthalpy of binding ($\Delta H$) is determined for the mixtures 78 and 79. This is accomplished by measuring the actual heat absorbed or released as a consequence of the binding reaction.

Next, as indicated by step 92, the heat capacities of both mixtures 78 and 79 are determined using the same temperatures as in step 84. Finally, as indicated by step 94, the equation $K_d = e^{-\Delta G/RT}$ is used to calculate the equilibrium binding constant. The process ends as indicated by step 95.

As stated above, many novel applications, other than that described above can be accomplished using the present invention. For example, large numbers of matched devices can be patterned on a single silicon wafer with all interconnections built in. A true lab-on-a-chip can be accomplished using the present invention.

Figure 6A:
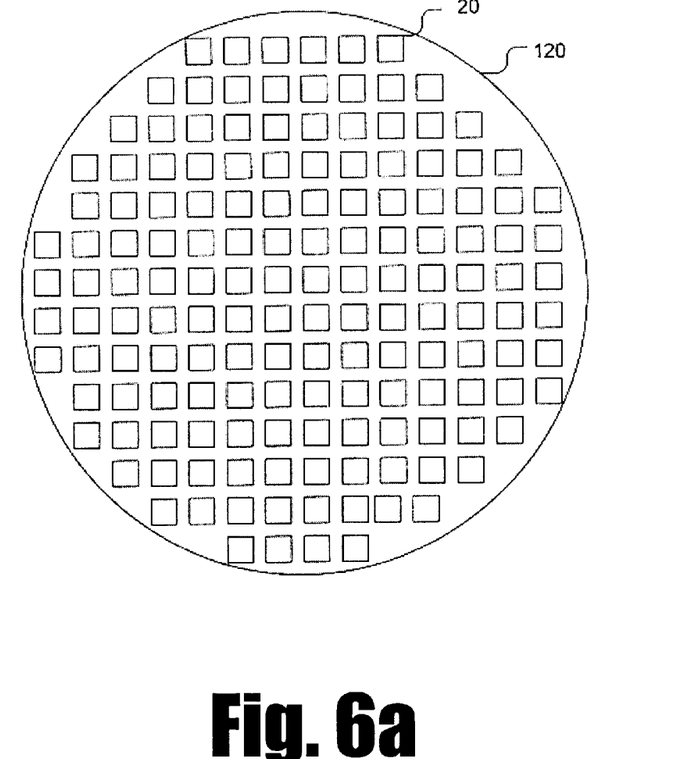
FIG. 6 depicts and example of an array of microcalorimeters in accordance with one embodiment of the present invention.
Figure 6B:
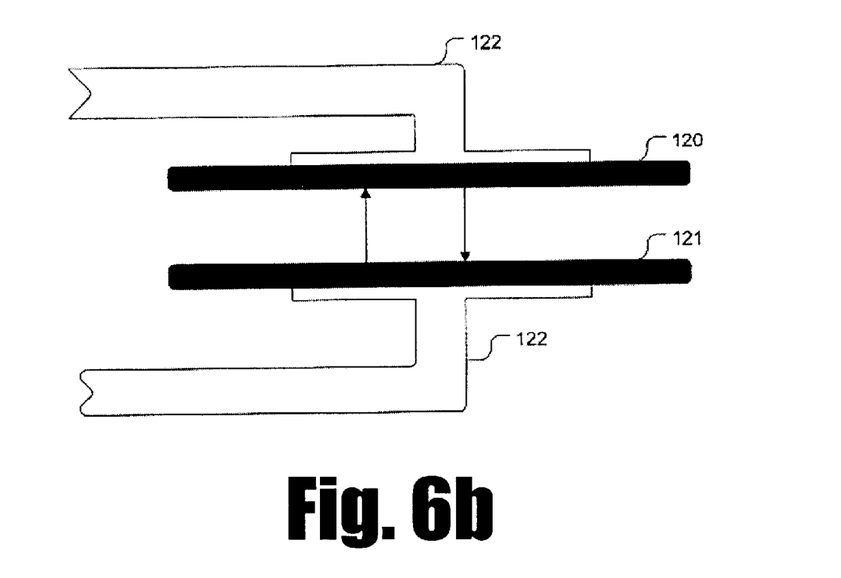

An example of an array of microcalorimeters is depicted n FIG. 6. The top portion of FIG. 6 depicts the operational side of a single wafer 120. The wafer 120 comprises a plurality of individual microcalorimeter devices 20. The bottom portion of FIG. 6 depicts a side view showing two wafers 120 and 121. As shown, the two wafers are oriented such that the operational side of one wafer 120 faces the operational side of the other wafer 121. Each wafer 120 and 121 is coupled to a robotic arm 122 which functions to couple the two wafers together.

Accordingly, in operation, each wafer 120 and 121 is oriented such that the operational side of the wafers 120 and 121 face each other. Robotic arms 122 are used to couple the wafers together for mixing. Typically, the robotic arms are used to align the wafers 120 and 121 with other devices as well, such as a device for dispensing solutions (not shown) and the like. The wafers 120 and 121 aligned so that so that each microcalorimeter device 20 in the top wafer 120 is exactly aligned with an associated microcalorimeter device 20 in the bottom wafer 121.

Thus, in this example, the configuration and arrangement of microcalorimeters 20 is exactly the same in the top and bottom wafers 120 and 121. It is noted that in other embodiments, this is not necessarily the case. However, when it is desired to mix samples in the manner described herein, it is essential that a matching pair of microcalorimeter devices 20 be precisely aligned in both the top and bottom wafers 120 and 121.

In this fashion, large-scale operations, such as high-throughput pharmaceutical drug screening can be accomplished most efficiently. As stated, any number of microcalorimeters 20 can be patterned on each device and is only limited by the fabrication technology and the size of the wafers used to implement an embodiment of the present invention.

As stated, many novel applications can be performed using the present invention. Listed below are several examples of such novel applications. This list is not intended to be exhaustive or limiting in any way, but is presented to point out some particular advantages of the present invention.

EXAMPLE 1

Calorimetric Screening

The present invention is well suited for this task due to the ability to perform many reactions simultaneously, and because a quantity of devices can be easily manufactured. One example of its use might is to find out what signaling pathways impinge on a putative transcriptional element. For example, scientists can test which pathways are involved by using arrays 120 of stopped flow type microcalorimeters.

This can be performed as follows. First, a drop of nuclear protein extract that contains constitutively activated factors corresponding to the different pathways is placed onto one side of a sandwich of different calorimeters 20 in an array 120. The DNA of interest is placed on the other side of the sandwich array 121. Control DNA of similar length, that is known not to be involved in the pathway being tested, is placed on cells 20 in the array 120, aligned with the extract on the other half of the sandwich 121.

Duplicate reactions of both the controls and samples are run to improve signal to noise. Since the only trigger is the addition of the DNA of interest, adding the curves of duplicate reactions will show a signal over the noise corresponding to the enthalpy change on binding. This way, not only is the pathway that impinges on the DNA sample found, but thermodynamic information of the binding is also learned. Automated drug screening is another example of the use of calorimeter arrays where binding information acquired during the screening process can help in candidate drug selection.

Titration Calorimetry Example

Titration calorimetry can be performed using arrays 120 of the microcalorimeter devices 20 in accordance with one embodiment of the present invention. A sample is placed in each of the calorimeters in the array 120. On the other half 121 of the sandwich, drops in known different concentrations are placed. When the sandwich 120 121 is closed, the enthalpy curves corresponding to the different concentrations are compared. The drop concentration where no more heat is evolved is analogous to the point at which no additional heat is released with further titration. This can be fine-tuned since the masses of both the drop size and the sample are known. Again these are balanced against solvent-sample mixing enthalpies and subtracted from the sample$_1$-sample$_2$ mixing enthalpy.

Multi-Component Calorimetry Example

The present invention can also be used to monitor the enthalpy of protein-protein/protein-DNA interactions using both the stopped-flow and titration calorimetric methods. A property of the present invention is that the internal time constant ($\tau_{int}$) is fast relative to conventional stopped-flow and titration calorimeters as described above. An interesting application of the present invention is the ability to look into the time domain of multi-component macromolecular binding interactions in more detail then possible using conventional devices. The ability to discern multi-component interactions via these methods is best appreciated given an example.

Suppose five proteins are purified from HPLC, and it is proposed that they make up a transcription complex on a segment of DNA that has been isolated. The present invention can be used to determine the order in which they bind.

For illustrative purposes a simple scenario can be examined. For example, suppose that these proteins bind in order, that is, protein 1 binds to DNA first, protein 2 binds next, and so on until the complex D12345 is formed. Each of these binding events occurs with some enthalpy change.

The order of binding can be determined by combining the proteins and DNA in groups of three in different ways. Given these parameters having 6 components, each sandwich having 3, then there are 10 ways to combine the components assuming that the sandwich halves are equivalent. When combined, there will be one thermogram that has the least number of binding curves corresponding to the D12345 grouping. To determine which of these binds first, use the groupings D1-2 and D2-1, the first will give you one curve and the other will give two as follows:

| Bottom Half | Top Half | Binding curves |
|---|---|---|
| D12 | 345 | 3 |
| D13 | 245 | 4 |
| D14 | 235 | 4 |
| D15 | 234 | 4 |
| D23 | 145 | 5 |
| D24 | 135 | 5 |
| D25 | 134 | 5 |
| D34 | 125 | 5 |
| D35 | 124 | 5 |
| D45 | 123 | 5 |
| To narrow down: | | |
| D1 | 2 | 1 |
| D2 | 1 | 2 |
| D12 | 3 | 1 |
| D12 | 4 | 0 |
| D12 | 5 | 0 |
| D123 | 4 | 1 |
| D123 | 5 | 0 |

All these reactions are balanced against controls and replicative reactions should be run, the curves added, and the signal:noise ratio improved (as $\sqrt{R}$ where R=number of replicative runs). This capacity is due to the short time constants of these devices. Further, as they get faster, better time resolution will be possible enabling the devices to be used to probe faster events. Additionally, these processes can be automated by having pipettor stations with a small amount of sample at each, and programming an XYZ stage so that the designated drops are placed on the proper devices.

Portable Sensor Example

The size of the microcalorimeter 20 makes it suitable for use as a portable sensor where it could be used to screen for disease, drugs, chemical compounds or any other sample where binding agents exist and a heat change is associated with binding. Detection of a sample is accomplished by known binding agents that are either conjugated to the conduction layer, or are free in solution before the sample is applied.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A method for determining thermodynamic properties of a chemical/biological sample using a system comprising an environmental chamber and a microelectronic calorimeter having a sample holder coupled to a thermometer, said method comprising the steps of:

equilibrating the environmental chamber such that a vapor pressure of a pressure-controlled vapor contained inside the chamber is within a predetermined threshold of a vapor pressure of the sample, wherein the sample and the pressure-controlled vapor are in direct fluid communication;

introducing the sample into the chamber by dispensing the sample onto the sample holder;

stimulating the sample; and determining one or more thermodynamic properties of the sample by using the thermometer to measure the temperature resulting from said stimulating step.

2. The method of claim 1, wherein said stimulating step is performed by adding a second sample to the chemical/biological sample.

3. The method of claim 1, wherein said microelectronic calorimeter further comprises an energy input device and said stimulating step is performed by inputting energy into the sample using the energy input device.

4. The method of claim 1, wherein said system further comprises a second microelectronic calorimeter having a second sample holder, said method further comprising the steps of:

introducing a second sample into the chamber by dispensing the second sample onto a second sample holder;

mixing the samples together; and using the thermometer to determine one or more additional thermodynamic properties related to the mixture.

5. The method of claim 4, wherein said mixing step is performed by sandwiching the first and second microcalorimeters together.

6. The method of claim 1, wherein said microelectronic calorimeter comprises:

a thin amorphous membrane anchored to a surrounding frame; and said sample holder comprises a thin thermally isolated thermal conduction layer deposited on a central portion of the membrane for holding samples on one side and coupled to the thermometer on the other side.

7. A method for determining a binding constant associated with the combination of a first and second sample, comprising the steps of:

equilibrating an environmental chamber such that the vapor pressure of the internal atmosphere is within a predefined threshold from the vapor pressure of the first and second samples;

introducing the first and second samples to the internal atmosphere of the chamber;

heating the first and second samples to determine a heat capacity of the first and second samples;

mixing the first and second samples to form a mixture;

determining an enthalpy of binding associated with the mixture;

heating the mixture to determine a heat capacity of the mixture; and calculating the binding constant associated with the combination of the first and second samples based on the heat capacity of the first and second samples, the enthalpy of binding of the mixture, and the heat capacity of the mixture.

8. The method of claim 7, wherein said introducing step is accomplished by performing the step of:

introducing the first and second samples to the internal atmosphere of the chamber; by dispensing the first sample onto a first microcalorimeter and the second sample onto a second microcalorimeter, wherein the first and second microcalorimeters comprise a thermometer and a heater coupled to a sample holder.

9. The method of claim 8, wherein said mixing step is accomplished by sandwiching the first and second calorimeters together.

10. The method of claim 8, wherein said first and second calorimeters comprise:

a thin amorphous membrane anchored to a surrounding frame; and a thin thermally isolated thermal conduction layer deposited on a central portion of the membrane for holding samples on one side and coupled to the heater and thermometer on the other side.

11. The method of claim 8, further comprising the step of:

introducing a pair of reference samples to the internal atmosphere of the chamber to compensate for systematic errors.

12. A system for determining thermodynamic properties of a first and a second sample comprising:

an environmental chamber for maintaining a vapor pressure equivalent to the vapor pressure of the samples;

a first cell comprising: a thermally isolated structure inside a frame; a thermometer mounted to said structure; and a sample surface for receiving the samples;

a second cell comprising: a thermally isolated structure inside a frame; a thermometer mounted to said structure; and a sample surface for receiving said samples; and means for moving said first and second cells towards each other such that said sample surfaces are sufficiently proximate to combine said first and second samples.

13. The system of claim 12, wherein said means for moving said first and second cells towards each other comprises:

a clamshell device having an upper half and a lower half hingedly secured together, wherein said first cell is coupled to the inside surface of said upper half, and said second cell is coupled to the inside surface of said lower half, and said first cell and said second cells are aligned such that said first sample mixes with said second sample when said clamshell device is in a closed position.

14. A system for determining thermodynamic properties of a first set of samples comprising:
   a environmental chamber for maintaining a vapor pressure similar to the vapor pressure of the first set of samples;
   a first array comprising a wafer comprising a plurality of calorimeters for holding the first set of samples;
   wherein each calorimeter comprises:
      a thermally isolated structure inside a frame;
      a thermometer mounted to said structure; and
      a sample surface for receiving said samples.

15. The system of claim 14, further comprising:
   a second array comprising a wafer comprising a plurality of calorimeters for holding a second set of samples; and
   means for mixing the first and second set of samples by sandwiching said first and second arrays together.

16. The system of claim 15, wherein each of said calorimeters further comprise:
   an energy input device coupled to said thermally isolated structure.

17. The system of claim 16, where in said energy input device is a heater.

18. The system of claim 16, wherein said energy input device and said thermometer are coupled to one side of said thermally isolated structure and said samples are placed on the other side.

19. A system for determining thermodynamic properties of a first chemical/biological sample comprising:
   an environmental chamber adapted such that a vapor pressure of a pressure-controlled vapor contained inside the chamber is within a predetermined threshold of a vapor pressure of the first sample, wherein said first sample and said pressure-controlled vapor are in direct fluid communication; and
   a first microelectronic calorimeter comprising:
      a thin amorphous membrane anchored to a surrounding frame;
      a thin thermally isolated thermal conduction layer coupled to a central portion of said membrane for holding samples; and
      a thermometer coupled to said thermal conduction layer.

20. The system of claim 19, further comprising an energy input device coupled to said thermal conduction layer.

21. The system of claim 19, further comprising:
   a second microelectronic calorimeter similar to said first microelectronic calorimeter for holding a second chemical/biological sample; and
   means for mixing said first and second samples by sandwiching the first and second microcalorimeters together.

22. The system of claim 19, wherein said thin amorphous membrane is fabricated using Silicon Nitride ($Si_3N_4$).

23. The system of claim 19, wherein said frame is fabricated using Silicon.

24. The system of claim 20, wherein said energy input device is a heater.

25. The system of claim 24, wherein said thermometer and heater are placed on one side of the thermal conduction layer and the samples are placed on the other side of the thermal conduction layer.

* * * * *

UNITED STATES PATENT AND TRADEMARK OFFICE
CERTIFICATE OF CORRECTION

PATENT NO.   : 6,193,413 B1
DATED        : February 27, 2001
INVENTOR(S)  : David S. Lieberman It is certified that error appears in the above-identified patent and that said Letters Patent is hereby corrected as shown below:

Column 15, claim 1,
Lines 32-33, change "fluid communication" to -- contact --.

Column 18, claim 19,
Line 6, change "fluid communication" to -- contact --.

Signed and Sealed this

Fifth Day of February, 2002

*Attest:*

JAMES E. ROGAN
*Attesting Officer*       *Director of the United States Patent and Trademark Office*